US006200594B1

(12) United States Patent
Ernest et al.

(10) Patent No.: US 6,200,594 B1
(45) Date of Patent: Mar. 13, 2001

(54) BREAST-ENHANCING, HERBAL COMPOSITIONS AND METHODS OF USING SAME

(75) Inventors: Joseph Michael Ernest, Oceanside; Allen Smith, Encino, both of CA (US)

(73) Assignee: Vital Dynamics, Inc., Canoga Park, CA (US)

( * ) Notice: Subject to any disclaimer, the term of this patent is extended or adjusted under 35 U.S.C. 154(b) by 0 days.

(21) Appl. No.: 09/473,693

(22) Filed: Dec. 29, 1999

(51) Int. Cl.$^7$ .................................................. A61K 47/00
(52) U.S. Cl. ........................... 424/439; 424/400; 424/449
(58) Field of Search ............................ 424/9.1, 400, 439, 424/441, 444, 449

(56) References Cited

U.S. PATENT DOCUMENTS

| | | |
|---|---|---|
| 4,460,488 | 7/1984 | Grollier et al. . |
| 4,569,839 | 2/1986 | Grollier et al. . |
| 4,767,618 | 8/1988 | Grollier et al. . |
| 4,933,177 | 6/1990 | Grollier et al. . |
| 5,407,677 | 4/1995 | Grollier et al. . |
| 5,494,668 | 2/1996 | Patwardhan . |
| 5,565,199 | 10/1996 | Page et al. . |
| 5,569,459 | 10/1996 | Shlyankevich . |
| 5,658,580 | 8/1997 | Mausner . |
| 5,683,698 | 11/1997 | Chavali et al. . |
| 5,707,630 | 1/1998 | Morrow . |
| 5,788,953 | 8/1998 | Somlyai . |
| 5,788,971 | 8/1998 | Togasaki . |
| 5,804,168 | 9/1998 | Murad . |
| 5,817,329 | 10/1998 | Gardiner . |
| 5,854,291 | 12/1998 | Laughlin et al. . |
| 5,869,540 | 2/1999 | Smith . |
| 5,874,084 | 2/1999 | Yng-Wong . |
| 5,888,514 | 3/1999 | Weisman . |
| 5,891,440 | 4/1999 | Lansky . |
| 5,908,628 | 6/1999 | Hou . |
| 5,910,307 | 6/1999 | Kwak et al. . |
| 5,916,565 | 6/1999 | Rose et al. . |
| 5,962,018 | 10/1999 | Curtis et al. . |
| 5,968,518 | 10/1999 | Pike . |

Primary Examiner—Dameron Jones

(57) ABSTRACT

Topical and oral compositions containing unique blends of certain herbs effectively enhance breasts in human females by strengthening connective tissues and encouraging the growth of new cells. The topical composition contains Saw Palmetto berry extract, Chaste Tree berry extract, Fenugreek seed extract, Fennel seed extract, Comfrey extract, White Willow Bark extract, Ma Huang extract, Black Cohosh extract, Guarana extract, Passion Flower extract, Bilberry extract, Horsetail extract and Cayenne extract. The oral composition is a dietary supplement system containing two diet supplement compositions. The first composition contains extracts of Blessed Thistle, Hops, Wild Yam, Fenugreek seed, Saw Palmetto berry, Chaste Tree berry, Fennel seed, Black Cohosh, Damiana, Dong Quai, Lycium Chinese Herb, Scullcap Concentrate, and Curcubita Pepo Pumpkin seed, as well as Methyl Sulfonyl Methane and Royal Jelly. The second composition contains extracts of Saw Palmetto berry, Chaste Tree berry, Black Cohosh, Fennel seed, Fenugreek seed, Lycium Chinese Herb, Scullcap Concentrate, and Curcubita Pepo Pumpkin seed, as well as Methyl Sulfonyl Methane and Royal Jelly. The topical composition, which is preferably in cream form, is topically applied to the breast area daily for a sufficient period of time. The oral system, preferably in the form of a plurality of capsules taken separately, is orally administered on a daily basis for a sufficient period, wherein capsules of the first composition are taken for a first period and capsules of the second composition are taken for a subsequent second period. Most preferably, the topical and oral compositions are administered concurrently in a treatment regimen. The latter regimen provides a synergistic breast enhancement relative to the individual topical and oral treatments.

18 Claims, No Drawings

BREAST-ENHANCING, HERBAL COMPOSITIONS AND METHODS OF USING SAME

BACKGROUND OF THE INVENTION

The present invention relates to compositions and methods for enhancing breasts. More particularly, this invention relates to herbal topical and oral compositions and methods of using same to enhance breast appearance in women.

An attractive bustline is important to many women. Unfortunately, as women age, lose weight or become inactive, their bustlines tend to become less firm and, therefore, less attractive.

The strengthening or building up of biological tissue in the female human breast is a well known problem in physiotherapy. One medical approach uses surgical techniques, such as breast implant operations. Such approach has numerous disadvantages. For example, surgical operations are inherently dangerous and relatively expensive. Opting for use of a surgical breast implant carries with it not only the danger and expense involved in any surgical operation but also potential health dangers that may be associated with using a particular type of breast implant, namely, the silicone breast implant.

Another medical approach for strengthening breast tissue involves hydrotherapy, wherein jets of pulsating water are directed to impinge upon the breast tissue. This approach is disadvantageous in that breast tissue is rather delicate and is easily damaged by such pulsating jets.

Yet another medical approach for strengthening breast tissue involves the use of external creams or internal hormone preparations. However, these compositions have been found either to be ineffective or to cause harmful side effects.

Many women who wish to enhance their breast appearance in a non-permanent and health risk-free manner opt to use an externally worn article, e.g., a foam pad. However, such articles frequently look unnatural and feel foreign, thereby diminishing any self image or amount of confidence a user may have in their physical appearance.

Thus, it would be desirable to provide a means for providing a firm bustline in women which does not involve breast implants or any other surgical technique, does not damage the breast tissue, is not an externally-worn article, and is effective without causing harmful side effects.

Natural ingredients, particularly herbs, have been used to treat various conditions in humans.

For example, herbs have been used to reduce bone and joint inflammation. Reference is made, e.g., to U.S. Pat. Nos. 5,494,668, 5,683,698, 5,916,565, 5,888,514, 5,908,628; 5,788,971; 5,854,291; and 5,910,307.

Herbs have also been used to relieve symptoms associated with female hormonal imbalances. See, e.g., U.S. Pat. Nos. 5,569,459; 5,707,630; 5,891,440; 5,565,199; 5,968,518, and 5,874,084).

Wild Yam liquid extract, Black Cohosh, and various other herbs have been used in progesterone creams to treat premenstrual syndrome, menopause and hot flashes and to prevent osteoporosis. Another cream, known as "ProYam Cream" because it contains Yam extract, is also said to be useful for treating PMS, menopause, and osteoporosis. A menopause-treating body cream available under the designation Emerita™ and referred to as a phytoestrogen body cream includes, among other ingredients, Dong Quai extract, Black Cohosh extract, and Chaste Tree Berry extract. Another cream for treating PMS and menopausal symptoms, referred to in an advertisement as "Feminease Cream" includes Wild Yam extract, Black Cohosh root, and various other herbs. A supplement known as "Feminique Supplement" which can be taken with the Feminease Cream contains Damiana leaves, Saw Palmetto berries, Dong Quai root, Capsicum fruit, along with other ingredients. A dietary supplement commercially available under the designation Super-Plus™ "Physician's Formula" includes, among other ingredients, Wild Yam extract, Black Cohosh powder, and Fennel seed powder, and features diosgenin, a precursor to the hormone dehydroepiandrosterone (DHEA.).

In addition, herbs have been used to treat skin or hair in humans. Reference is made, for example, to U.S. Pat. Nos. 4,460,488, 4,569,839, 4,767,618, 4,933,177, 5,407,677, 5,658,580, 5,869,540, 5,804,168, 5,788,953 and 5,962,018.

Herbs have also been used in nutritional supplements designed to promote muscle adaptation to strenuous exercise. See, e.g., U.S. Pat. No. 5,817,329.

The human body is able to identify the chemical components in which it is deficient. An interesting and important feature of herbal interaction with the human body is the fact that the body will only absorb from an herbal compound those chemical components in which the body is deficient. Those chemical components of the herbal compound which are not needed simply pass through the body without undue stress placed on the body.

Thus, the benefits associated with the use of herbs makes it continually desirable to use herbal compositions to treat disorders in humans.

A primary object of this invention is to provide an herbal composition which is effective in enhancing breasts in women and which does so without harmful side effects.

A further object of this invention is to provide the aforementioned composition in the form of a topically applied product.

A still further object of this invention is to provide the composition set forth in the stated first object of this invention in the form of an orally administered product.

Another object of this invention is to provide methods of enhancing breasts in women using the compositions described in the preceding objects.

These and other objects are achieved in the present invention.

SUMMARY OF THE INVENTION

The present invention provides safe and effective natural-ingredient compositions and methods of using same to enhance breasts in women.

A first breast-enhancing composition within the scope of the present invention is a topically administered composition containing effective amounts of the following natural ingredients:

(1) Saw Palmetto berry extract;
(2) Chaste Tree berry extract;
(3) Fenugreek seed extract;
(4) Fennel seed extract;
(5) Comfrey extract;
(6) White Willow bark;
(7) Ma Huang extract;
(8) Black Cohosh extract;
(9) Guarana extract;
(10) Passion Flower extract;
(11) Bilberry extract;

(12) Horsetail extract; and

(13) Cayenne extract.

A second breast-enhancing composition of the present invention is a dietary supplement composition system composed of two compositions which are to be taken separately. The first composition contains effective amounts of the following natural ingredients:

(1) Blessed Thistle extract;
(2) Hops extract;
(3) Wild Yam root extract;
(4) Fenugreek seed extract;
(5) Saw Palmetto berry extract;
(6) Chaste Tree berry extract;
(7) Fennel seed extract;
(8) Damiana extract;
(9) Dong Quai extract;
(10) Methyl Sulfonyl Methane;
(11) Lycium Chinese Herb extract;
(12) Black Cohosh root extract;
(13) Royal Jelly;
(14) Scullcap Concentrate extract; and
(15) Curcubita Pepo Pumpkin seed extract.

The second composition of the two-part system contains effective amounts of the following natural ingredients:

(1) Saw Palmetto berry extract;
(2) Fenugreek seed extract;
(3) Chaste Tree berry extract;
(4) Fennel seed extract;
(5) Methyl Sulfonyl Methane;
(6) Lycium Chinese Herb extract;
(7) Black Cohosh extract;
(8) Royal Jelly,
(9) Scullcap Concentrate extract; and
(10) Curcubita Pepo Pumpkin seed extract.

The present invention is also directed to methods of enhancing the breasts in women, using the aforementioned compositions.

Thus, one method of the present invention involves the step of topically administering to the breast area of a woman the topical composition of this invention. The composition is applied daily for a sufficient period of time.

A second method of the present invention involves the following steps:

(a) orally administering to the female on a daily basis during a first period of time an effective daily dosage of the first diet supplement composition; and (b) orally administering to the female on a daily basis during a second period of time an effective daily dosage of the second diet supplement composition, wherein the second diet supplement composition is administered independently of the first diet supplement composition, further wherein the second period of time is subsequent to the first period of time.

The two parts of the oral composition are most preferably in the form of two separate and distinct capsules.

In the most preferred regimen for enhancing the breasts in accordance with the present invention, the topical and oral compositions are concurrently administered. Such concurrent use of the topical and oral compositions has been found to synergistically increase the breast-enhancing properties of the topical and oral compositions taken individually.

Both the topically administered and the orally administered herbal compositions of this invention are are safe to use and easy to administer.

A particular advantage of the topical composition of this invention is that it does not stain clothing, thereby allowing the user to dress immediately following application.

DETAILED DESCRIPTION OF THE INVENTION

As stated hereinabove, the present invention provides safe and effective compositions and methods for enhancing breasts in women. As used herein with respect to the compositions' and methods' effect on the breasts, the terms "enhance", "enhances" and "enhancing" means that the compositions and the methods help to firm and support the breasts and improve muscle tone. The compositions and methods enhance the breasts by strengthening connective tissues and encouraging the growth of new cells.

The compositions of this invention contain a unique blend of natural ingredients.

The topically administered composition of this invention contains effective amounts of Saw Palmetto berry extract, Chaste Tree berry extract, Fenugreek seed extract, Fennel seed extract, Comfrey extract, White Willow Bark extract, Ma Huang extract, Black Cohosh extract, Guarana extract, Passion Flower extract, Bilberry extract, Horsetail extract, and Cayenne extract.

The orally administered composition of this invention is in the form of a two-composition diet supplement system, wherein the two diet supplement compositions are taken separately and during different time periods. The first composition contains effective amounts of Blessed Thistle extract, Hops extract preferably concentrated 4:1), Wild Yam root extract, Fenugreek seed extract, Saw Palmetto berry extract, Chaste Tree berry extract, Fennel seed extract, Black Cohosh extract, Damiana extract, Dong Quai extract, Methyl Sulfonyl Methane (MSM), Lycium Chinese Herb (wolfberry) extract (preferably concentrated 10:1), Royal Jelly, Scullcap root concentrate extract and Curcubita Pepo Pumpkin seed extract. The second diet supplement composition is composed of effective amounts of Saw Palmetto berry extract, Chaste Tree berry extract, Black Cohosh extract, Fennel seed extract, Fenugreek seed extract, Lycium Chinese Herb (wolfberry) extract, Methyl Sulfonyl Methane (MSM), Scullcap root concentrate extract, Curcubita Pepo Pumpkin seed extract, and Royal Jelly.

A primary advantage of the present invention is its use of several herbs which contain phytoestrogens. Phytoestrogens are naturally occurring chemicals derived from plants and have an estrogen-like effect in the body and a structural similarity to estrogens made by the body. Specific phytoestrogens include diosgenin, beta-sitosterol, isoflavones, and coumestans. The phytoestrogens used in the present invention appear to play a major role in the breast-enhancing properties of the compositions of the invention.

The phytoestrogen-containing herbs used in the present invention include Black Cohosh (isoflavones), Fennel (anethole), Wild Yam (diosgenin), Fenugreek (diosgenin), Damiana, Dong Quai, and Chaste Tree Berry.

The other herbal and non-herbal components used in the present invention also provide therapeutic benefits.

Saw Palmetto (*Serenoa repens*) berries have been used to treat benign prostate enlargement, menstrual cramps, urinary tract problems, impotency in both men and women, and to increase appetite. The berries contain fatty acids and phytosterols.

The roots and leaves of the Comfrey (*Symphytum officinale*, Linn.) plant have been used medicinally. The Comfrey root contains mucilage, allantoin, a small amount of tannin, and a very small amount of starch, and has been used to treat coughs. The Comfrey leaves are used as an external remedy for sprains, swellings, bruises, cuts, boils, abscesses, and ulcers. The whole plant has been used to sooth pain associated with inflammation.

White Willow Bark (botanical name: Salix alba) contains tannin as its chief constituent, as well as a small amount of salicin. It is frequently administered as a painkiller and is believed to be a natural precursor to aspirin. It is commonly used to treat rheumatism, fever, headaches and pain caused by inflammation.

Ma Huang (*Ephedra sinica*), a source of ephedrine, is a mild energizing herb that suppresses appetite, promotes thermogenic metabolism, increases perspiration and stimulates the nervous system. It is widely used for upper respiratory tract ailments and in many natural cold remedies. For medicinal uses, the whole plant (in dried and powdered form) can be used, or the stems alone can be used. In the present invention, extracts of the Ma Huang stem are preferably used.

The seeds of the Guarana (*Paullinia Cupana*, Kunth.) plant contains guaranine which is chemically identical to caffeine. The Guarana seeds are used to treat headaches and the distress that accompanies menstruation.

Passion Flower (*Passiflora incarnata*) contains alkaloids and flavenoids which help induce sleep and relaxation. Passion flower has also been used to treat menstrual cramps. The medicinal parts of the plant are the leaves, stems, flowers and fruit.

The parts of the Bilberry (*Vaccinium mryritillus*, Linn.) plant used medicinally are the leaves and the berries. The leaves contain quinic acid and a small amount of tannin. The berries contain high amounts of the flavenoid complex anthocyanosides which exhibit potent antioxidant activity. Anthocyanosides support normal formation of connective tissue and strengthen capillaries in the body.

Horsetail (*Equisetum arvense*) are useful in shrinking tissues and preventing secretion of fluids. Horsetail extracts are generally prepared from the barren stems of the plant.

Cayenne (also known as capsicum), the active ingredient of which is capsaicin, has been used to stimulate circulation and enhance blood flow, to ease intestinal inflammation, and to buffer pain from menstrual cramps, arthritis, varicose veins and headaches. The whole cayenne plant is preferably used in the present invention.

Blessed Thistle (Cnicus benedictus), a plant found primarily in Asia and Europe, is a common component of herbal formulas used to relieve menstrual symptoms. In Europe, Blessed Thistle is regarded as an excellent appetite stimulant and is used in the manufacture of bitters to be taken before meals to stimulate stomach and intestinal activity and aid in digestion and circulation. It has also been used to treat constipation and flatulence, and is also considered to be an excellent heart tonic and blood purifier. The active constituents in Blessed Thistle are the sesquiterpene lactones (such as cnicin) which provide the main beneficial effects of the plant. The bitterness of these compounds stimulates digestive activity, including the flow of saliva and secretion of gastric juice, which leads to improved appetite and digestion. There is some evidence that Blessed Thistle also has anti-inflammatory properties. The leaves, stems and flowers of the plant are all used in herbal preparations.

Hops (*Humulus Lupulus*, Linn.) has been used to improve appetite and digestion and to promote sleep. As an external remedy, Hops has been used in combination with chamomile flowers or poppy heads to reduce painful swelling, inflammation, neuralgic and rheumatic pains, bruises, boils and gatherings. The flowers of the Hops plant are used medicinally. The Hops flowers contain a volatile oil which consists chiefly of the sesquiterpene Humulene.

Methyl-sulfonyl-methane (MSM) is a naturally occurring organic source of biologically available nutritional sulfur. Sulfur is an integral part of many proteins, hormones and other substances critical to healthy metabolism. MSM, which is found in most fresh fruits and vegetables, milk and grains, is a strong antioxidant and has been used, for example, to help keep hormones in balance, relieve stress and constipation, fight against candida, asthma, emphysema, arthritis, and tendonitis, reduce muscle cramps and back pain, increase heart function and blood circulation, strengthen capillary walls and reduce varicose veins.

Lycium Chinese Herb(Wolfberry) is a vitamin-filled and mineral-filled antioxidant containing over 13% by weight of protein. It contains beta-carotene; vitamins B1, B2, B6, C and E; and 21 trace nutrients.

Royal Jelly, which is made by worker bees, is high in certain fatty acids, simple carbohydrates, and pantothenic acid.

Scullcaps (*Scutellaria lateriflora; Scutellaria baicalensis*) are a member of the mint family. *Scutellaria lateriflora* contains scutellarian which has mild sedative and antispasmodic actions. The root of the *Scutellaria baicalensis* plant contains a flavenoid substance, baicalin, which has a protective effect on the liver. *Scutellaria baicalensis* is also used in herbal combinations to treat inflammatory skin conditions, allergic diseases, high cholesterol and triglycerides, and high blood pressure. Preferably, the present invention uses an extract made from the root of the *Scutellaria baicalensis* plant.

As used herein with respect to certain of the herbs used in the present invention, the term "extract" means a concentrate of water-soluble and/or alcohol-soluble plant components from the portion of the plant extracted.

As used herein with respect to the amounts of the ingredients present in the compositions of this invention, the term "effective amount" means that amount of the ingredient which will contribute toward the overall composition's ability to provide a breast-enhancing effect.

The first and second diet supplement compositions are preferably each in the form of at least one separate and distinct capsule or tablet. Preferably, each composition is in the form of a plurality of capsules or tablets.

The herbs used in the present invention are preferably prepared for addition to the compositions by, for example, grinding, comminuting, etc. a particular portion of the herb and forming an extract by any known method, e.g., an aqueous or organic extract. For example, the extracts can be prepared by combining the dried and crushed plant with water or a mixture of water and a water-miscible organic solvent (preferably a mixture of ethanol and water) by steeping or boiling. The resulting extract is then filtered, leaving a solution of the active ingredient in the herb.

In the topical and oral compositions of the present invention, the saw palmetto extract is preferably taken from the berry portion of the saw palmetto herb, the chaste tree extract is preferably taken from the beny portion of the chaste tree herb, the fenugreek extract is preferably taken from the seed of the fenugreek herb, the fennel extract is preferably taken from the fennel seed, and the black cohosh extract is preferably taken from the root of the black cohosh herb.

In the topical composition of this invention, the comfrey extract is preferably taken from the root of the comfrey herb. The cayenne extract is preferably taken from the berry portion of the herb.

In the oral composition of this invention, the hops extract is preferably taken from the flower portion of the plant. The wild yam extract is preferably taken from the root of the plant. The damiana extract is preferably taken from the leaf of the plant. The extract of the dong quai herb is taken from the root. The skullcap concentrate extract is preferably taken from the root of the herb or from the entire herb. The extract of the curcubita pepo pumpkin is preferably taken from the seed of the plant.

The topical composition of this invention preferably includes a pharmaceutically acceptable carrier for topical administration. The topical composition can be in the form of a cream, a lotion, a gel, an ointment, a stick, a spray, a tape, a patch, or the like. Most preferably, the topical composition of this invention is in the form of a cream. The cream can be prepared according to known cream-forming methods. Reference is made, e.g., to U.S. Pat. No. 5,658,580, which is hereby incorporated by reference herein in its entirety.

The topical composition may contain one or more conventional ancillary ingredients used in conventional topical compositions. For example, the composition may contain one or more humectants, surfactants, preservatives, thickeners, fragrances, colorants, vitamins, retinoids, and/or emollients.

Suitable humectants include, e.g., glycerine, sorbitol, polyethylene glycol, collagen, and the like.

Suitable surfactants include, e.g., sodium stearyl sulfate, diethanolamine cetyl sulfate, polyethylene glycol isostearate, and the like.

Suitable preservatives include, e.g., methyl paraben, propyl paraben and the like.

Suitable vitamins include, e.g., vitamin B6, vitamin B12, vitamin D3, 1,25-dihydroxy vitamin D3, vitamin B1, vitamin B2, vitamin K, vitamin E, tocotrienols and their derivatives, nicotinic acid and its esters, pantothenic acid and its esters, panthenol, folic acid and its derivatives, choline, carnitine, and the like.

Suitable retinoids include, e.g., retinol, retinoic acid, retinyl palmitate, retinyl propionate, retinyl acetate, isotretonin, and the like.

Examples of suitable thickeners include xanthan gum, hydroxypropyl cellulose, hydroxyethyl cellulose, carbopol, gum acacia, vee-gum, and magnesium aluminum silicate.

Suitable emollients for use in the topical composition of this invention include, e.g., silicone oils (such as cyclomethicone/dimethicone copolyol and cyclotetramethicone), mineral oil, cocoa butter, fatty acid esters, beeswax, and lanolin.

In its most preferred embodiments, the topical composition of this invention includes caprylic/capric triglyceride, glycerin, aloe vera gel, stearic acid, cetyl alcohol, glyceryl stearate, PEG-100 stearate, dimethicone, soluble collagen, petrolatum, MSM, fragrance, peppermint oil, tocopheryl acetate, retinyl palmitate, zinc gluconate, triethanolamine, DMDM hydantoin, methyl paraben, propyl paraben, carbomer, and tetrasodium EDTA.

The oral dietary supplement system of this invention preferably includes a pharmaceutically acceptable carrier suitable for oral administration. Each composition in the system preferably takes the form of solid tablets or capsules.

The compositions may be prepared into the solid form by any conventional method. Reference is made, e.g., to U.S. Pat. Nos. 5,911,992 and 5,985,282, both of which are hereby incorporated by reference herein in their entirety.

Any carriers known in the art for oral application compositions may be used. For solid form preparations, such as, e.g., powders, tablets, and capsules, a solid carrier may be one or more substances such as diluents, flavoring agents, solubilizers, lubricants, suspending agents, binders, tablet-disintegrating agents, encapsulating materials, and the like. Suitable carrier materials may include, e.g., stearic acid, silica, magnesium carbonate, calcium carbonate, sodium bicarbonate, magnesium stearate, calcium stearate, talc, lactose, sugar, pectin, dextrin, starch, tragacanth, cellulose derivatives, methyl cellulose, sodium carboxymethyl cellulose, a low-melting wax, cocoa butter, alginates, gelatin, polyvinyl pyrrolidone, polyethyl glycols, quaternary ammonium compounds, and the like.

In the most preferred embodiment of the oral system of this invention, the two compositions are in the form of capsules. The most preferred carrier materials for use in the capsules include stearic acid, gelatin, silica and magnesium stearate.

The present invention also provides methods of using the topical and oral compositions of this invention to effect breast enhancement.

In accordance with the present invention, an effective amount of the topical composition is applied to the breasts and preferably also neck and shoulders and the area between the neck, shoulders and breasts. For improved results, a hot, moist towel is placed over the breasts for about five minutes after the cream has been applied. The breasts are then lightly toweled dry. Preferably, the topical composition is applied twice a day, more preferably once in the morning (after bathing) and once before bedtime. The topical composition is applied daily for a sufficient period of time to effect breast enhancement. Typically, the composition is applied daily for at least five months.

The daily dosage of the topical composition preferably contains:

(1) from about 15.0% to about 17.0% by weight of the Saw Palmetto extract;

(2) from about 12.0% to about 14.0% by weight of the Chaste Tree berry extract;

(3) from about 11.0% to about 13.0% by weight of the Fenugreek seed extract;

(4) from about 9.0% to about 11.0% by weight of the Fennel seed extract;

(5) from about 8.0% to about 10.0% by weight of the Comfrey extract;

(6) from about 8.0% to about 10.0% by weight of the White Willow bark extract;

(7) from about 7.0% to about 9.0% by weight of the Ma Huang extract;

(8) from about 5.0% to about 7.0% by weight of the Black Cohosh extract;

(9) from about 5.0% to about 7.0% by weight of the Guarana extract;

(10) from about 5.0% to about 7.0% by weight of the Passion Flower extract;

(11) from about 1.0% to about 3.0% by weight of the Baiberry extract;

(12) from about 1.0% to about 3.0% by weight of the Horsetail extract; and

(13) from about 0.5% to about 1.5% by weight of the Cayenne extract.

Most preferably, the daily dosage of the topical composition of this invention contains:

(1) about 16% by weight of the Saw Palmetto berry extract;
(2) about 13% by weight of the Chaste Tree berry extract;
(3) about 12% by weight of the Fenugreek seed extract;
(4) about 10% by weight of the Fennel seed extract;
(5) about 9% by weight of the Comfrey extract;
(6) about 9% by weight of the White Willow bark extract;
(7) about 8% by weight of the Ma Huang extract;
(8) about 6% by weight of the Black Cohosh extract;
(9) about 6% by weight of the Guarana extract;
(10) about 6% by weight of the Passion Flower extract;
(11) about 2% by weight of the Bilberry extract;
(12) about 2% by weight of the Horsetail extract; and
(13) about 1% by weight of the Cayenne extract.

For daily application, one-half of the daily dosage is preferably applied in the morning and the remaining one-half of the daily dosage is preferably applied at bedtime.

The oral dietary supplement system is administered as follows. For a first period of time, an effective daily dosage of the first diet supplement composition is orally administered to the female on a daily basis, and for a subsequent, second period of time, an effective daily dosage of the second diet supplement composition is orally administered to the female on a daily basis.

Preferably, the daily dosage of the first composition contains:

(1) from about 12.0% by weight to about 14.0% by weight of the Blessed Thistle extract;
(2) from about 12.0% by weight to about 14.0% by weight of the Hops extract;
(3) from about 10.0% by weight to about 12.0% by weight of the Wild Yam Root extract;
(4) from about 8.0% by weight to about 10.0% by weight of the Fenugreek seed extract;
(5) from about 8.0% by weight to about 10.0% by weight of the Saw Palmetto berry extract;
(6) from about 7.0% by weight to about 9.0% by weight of the Chaste Tree berry extract;
(7) from about 7.0% by weight to about 9.0% by weight of the Fennel seed extract;
(8) from about 6.0% by weight to about 8.0% by weight of the Damiana extract;
(9) from about 4.0% by weight to about 6.0% by weight of the Dong Quai extract;
(10) from about 3.0% by weight to about 5.0% by weight of the Methyl Sulfonyl Methane;
(11) from about 3.0% by weight to about 5.0% by weight of the Lycium Chinese Herb extract;
(12) from about 6.0% by weight to about 8.0% by weight of the Black Cohosh extract;
(13) from about 1.0% by weight to about 3.0% by weight of the Royal Jelly,
(14) from about 0.5% by weight to about 1.5% by weight of the Scullcap Concentrate extract; and
(15) from about 0.5% by weight to about 1.5% by weight of the Curcubita Pepo Pumpkin seed extract.

Most preferably, the daily dosage of the first composition contains:

(1) about 12.0% by weight of the Blessed Thistle extract;
(2) about 12.0% by weight of the Hops extract;
(3) about 11.0% by weight by weight of the Wild Yam Root extract;
(4) about 9.0% by weight of the Fenugreek seed extract;
(5) about 9.0% by weight of the Saw Palmetto berry extract;
(6) about 8.0% by weight of the Chaste Tree berry extract;
(7) about 8.0% by weight of the Fennel seed extract;
(8) about 7.0% by weight of the Damiana extract;
(9) about 5.0% by weight of the Dong Quai extract;
(10) about 4.0% by weight of the Methyl Sulfonyl Methane;
(11) about 4.0% by weight of the Lycium Chinese Herb extract;
(12) about 7.0% by weight of the Black Cohosh extract;
(13) about 2.0% by weight of the Royal Jelly,
(14) about 1.0% by weight of the Scullcap Concentrate extract; and
(15) about 1.0% by weight of the Curcubita Pepo Pumpkin seed extract.

The daily dosage of the second diet supplement composition preferably contains:

(1) from about 20.0% by weight to about 22.0% by weight of Saw Palmetto berry extract;
(2) from about 14.0% by weight to about 16.0% by weight of Fenugreek seed extract;
(3) from about 11.0% by weight to about 13.0% by weight of Chaste Tree berry extract;
(4) from about 12.0% by weight to about 14.0% by weight of Fennel seed extract;
(5) from about 6.0% by weight to about 8.0% by weight of Methyl Sulfonyl Methane;
(6) from about 8.0% by weight to about 10.0% by weight of Lycium Chinese Herb extract;
(7) from about 7.0% by weight to about 9.0% by weight of Black Cohosh extract;
(8) from about 2.0% by weight to about 4.0% by weight of Royal Jelly;
(9) from about 6.0% by weight to about 8.0% by weight of Scullcap concentrate extract; and
(10) from about 4.0% by weight to about 6.0% by weight of Curcubita Pepo Pumpkin seed extract.

Most preferably, the daily dosage of the second diet supplement composition contains:

(1) about 21.0% by weight of Saw Palmetto berry extract;
(2) about 15.0% by weight of Fenugreek seed extract;
(3) about 12.0% by weight of Chaste Tree berry extract;
(4) about 13.0% by weight of Fennel seed extract;
(5) about 7.0% by weight of Methyl Sulfonyl Methane;
(6) about 9.0% by weight of Lycium Chinese Herb extract;
(7) about 8.0% by weight of Black Cohosh extract;
(8) about 3.0% by weight of Royal Jelly;
(9) about 7.0% by weight of Scullcap concentrate extract; and
(10) about 5.0% by weight of Curcubita Pepo Pumpkin seed extract.

For daily application, the daily dosage of the first composition is preferably divided into a plurality of sub-doses, each sub-dose being in the form of a tablet or capsule.

Preferably, a number of sub-dose capsules or tablets is taken in the morning and a number of sub-dose capsules or tablets is again taken at bedtime. Preferably, the first composition is applied daily for a period of at least two months, wherein four sub-dose capsules are administered in the morning and five sub-dose capsules are taken at bedtime. The capsules should be taken on an empty stomach or at least thirty minutes before eating. Each capsule should be taken with water.

For daily application during the second period of time, the daily dosage of the second composition is also preferably divided into a plurality of sub-doses, each sub-dose being in the form of a tablet or capsule. Also preferably, a number of sub-dose capsules or tablets is taken in the morning and a number of sub-dose capsules or tablets is again taken at bedtime. Preferably, the second composition is applied daily for a period of at least four months, wherein during the first month four sub-dose capsules are administered in the morning and five sub-dose capsules are taken at bedtime; during the second month, three sub-dose capsules are taken in the morning and four sub-dose capsules are taken at bedtime; and during the last two months, two sub-dose capsules are taken in the morning and two sub-dose capsules are taken at bedtime. The capsules should be taken on an empty stomach or at least thirty minutes before eating. Each capsule should be taken with water.

The period of time in which the second composition is administered is subsequent to the period of time the first composition is administered. Thus, preferably, the first composition is applied for the first two months and the second composition is applied for the next four months.

In a further embodiment, the present invention provides a method of enhancing the breasts in human females, wherein the method involves concurrent application of the topical and oral compositions of this invention. In this combined method, the user, on a daily basis, topically applies the topical composition in accordance with the method described hereinabove and also ingests the first dietary supplement composition during the first period of time and the second dietary supplement composition during the second period of time. For example, in a preferred six-month treatment regimen, the user topically applies the cream twice a day for five months, and injests the first diet supplement capsules daily for two months and the second diet supplement capsules for the subsequent four months.

The topical and oral compositions of this invention effectively enhance breasts in human females and do so without harmful side effects. Thus, the present invention provides a safe and effective way to promote a healthy breast appearance in women.

What is claimed is:

1. A topically administered composition for enhancing breasts of a human female, comprising:
   (1) an effective amount of a Saw Palmetto berry extract;
   (2) an effective amount of a Chaste Tree berry extract;
   (3) an effective amount of a Fenugreek seed extract;
   (4) an effective amount of a Fennel seed extract;
   (5) an effective amount of a Comfrey extract;
   (6) an effective amount of a White Willow Bark extract;
   (7) an effective amount of a Ma Huang extract;
   (8) an effective amount of a Black Cohosh extract;
   (9) an effective amount of a Guarana extract;
   (10) an effective amount of a Passion Flower extract;
   (11) an effective amount of a Bilberry extract;
   (12) an effective amount of a Horsetail extract; and
   (13) an effective amount of a Cayenne extract.

2. A composition according to claim 1, wherein the composition comprises:
   (1) from about 15.0% to about 17.0% by weight of the Saw Palmetto berry extract;
   (2) from about 12.0% to about 14.0% by weight of the Chaste Tree berry extract;
   (3) from about 11.0% to about 13.0% by weight of the Fenugreek seed extract;
   (4) from about 9.0% to about 11.0% by weight of the Fennel seed extract;
   (5) from about 8.0% to about 10.0% by weight of the Comfrey extract;
   (6) from about 8.0% to about 10.0% by weight of the White Willow Bark extract;
   (7) from about 7.0% to about 9.0% by weight of the Ma Huang extract;
   (8) from about 5.0% to about 7.0% by weight of the Black Cohosh extract;
   (9) from about 5.0% to about 7.0% by weight of the Guarana extract;
   (10) from about 5.0% to about 7.0% by weight of the Passion Flower extract;
   (11) from about 1.0% to about 3.0% by weight of the Bilberry extract;
   (12) from about 1.0% to about 3.0% by weight of the Horsetail extract; and
   (13) from about 0.5% to about 1.5% by weight of the Cayenne extract.

3. A composition according to claim 1, wherein the composition further comprises a pharmaceutically acceptable carrier.

4. A composition according to claim 1, wherein the composition is in the form of a cream.

5. A method of enhancing breasts of a human female, comprising the step of topically administering to the breasts of the female a daily dosage of a composition comprising:
   (1) an effective amount of a Saw Palmetto berry extract;
   (2) an effective amount of a Chaste Tree berry extract;
   (3) an effective amount of a Fenugreek seed extract;
   (4) an effective amount of a Fennel seed extract;
   (5) an effective amount of a Comfrey extract;
   (6) an effective amount of a White Willow Bark extract;
   (7) an effective amount of a Ma Huang extract;
   (8) an effective amount of a Black Cohosh extract;
   (9) an effective amount of a Guarana extract;
   (10) an effective amount of a Passion Flower extract;
   (11) an effective amount of a Bilberry extract;
   (12) an effective amount of a Horsetail extract; and
   (13) an effective amount of a Cayenne extract,
      wherein the composition is applied for an effective period of time.

6. A method according to claim 5, wherein the composition comprises:
   (1) from about 15.0% to about 17.0% by weight of the Saw Palmetto berry extract;
   (2) from about 12.0% to about 14.0% by weight of the Chaste Tree berry extract;
   (3) from about 11.0% to about 13.0% by weight of the Fenugreek seed extract;
   (4) from about 9.0% to about 11.0% by weight of the Fennel seed extract;
   (5) from about 8.0% to about 10.0% by weight of the Comfrey extract;

(6) from about 8.0% to about 10.0% by weight of the White Willow Bark extract;
(7) from about 7.0% to about 9.0% by weight of the Ma Huang extract;
(8) from about 5.0% to about 7.0% by weight of the Black Cohosh extract;
(9) from about 5.0% to about 7.0% by weight of the Guarana extract;
(10) from about 5.0% to about 7.0% by weight of the Passion Flower extract;
(11) from about 1.0% to about 3.0% by weight of the Bilberry extract;
(12) from about 1.0% to about 3.0% by weight of the Horsetail extract; and
(13) from about 0.5% to about 1.5% by weight of the Cayenne extract.

7. A method according to claim 5, wherein the composition further comprises a pharmaceutically acceptable carrier.

8. A method according to claim 5, wherein the composition is in the form of a cream.

9. A method according to claim 5, wherein the period of time is at least about five months.

10. A dietary supplement system for enhancing breasts of a human female, comprising:
(A) a first diet supplement composition containing:
(1) an effective amount of a Blessed Thistle extract;
(2) an effective amount of a Hops extract;
(3) an effective amount of a Wild Yam extract;
(4) an effective amount of a Fenugreek seed extract;
(5) an effective amount of a Saw Palmetto berry extract;
(6) an effective amount of a Chaste Tree berry extract;
(7) an effective amount of a Fennel seed extract;
(8) an effective amount of a Damiana extract;
(9) an effective amount of a Dong Quai extract;
(10) an effective amount of Methyl Sulfonyl Methane;
(11) an effective amount of a Lycium Chinese Herb extract;
(12) an effective amount of a Black Cohosh extract;
(13) an effective amount of Royal Jelly;
(14) an effective amount of a Scullcap Concentrate extract; and
(15) an effective amount of a Curcubita Pepo Pumpkin seed extract; and
(B) a second diet supplement composition, comprising:
(1) an effective amount of a Saw Palmetto berry extract;
(2) an effective amount of a Fenugreek seed extract;
(3) an effective amount of a Chaste Tree berry extract;
(4) an effective amount of a Fennel seed extract;
(5) an effective amount of Methyl Sulfonyl Methane;
(6) an effective amount of a Lycium Chinese Herb extract;
(7) an effective amount of a Black Cohosh extract;
(8) an effective amount of Royal Jelly;
(9) an effective amount of a Scullcap concentrate extract; and
(10) an effective amount of a Curcubita Pepo Pumpkin seed extract.

11. A system according to claim 10, wherein the first diet supplement composition comprises:
(1) from about 12.0% by weight to about 14.0% by weight of the Blessed Thistle extract;
(2) from about 12.0% by weight to about 14.0% by weight of the Hops extract;
(3) from about 10.0% by weight to about 12.0% by weight of the Wild Yam extract;
(4) from about 8.0% by weight to about 10.0% by weight of the Fenugreek seed extract;
(5) from about 8.0% by weight to about 10.0% by weight of the Saw Palmetto berry extract;
(6) from about 7.0% by weight to about 9.0% by weight of the Chaste Tree berry extract;
(7) from about 7.0% by weight to about 9.0% by weight of the Fennel seed extract;
(8) from about 6.0% by weight to about 8.0% by weight of the Damiana extract;
(9) from about 4.0% by weight to about 6.0% by weight of the Dong Quai extract;
(10) from about 3.0% by weight to about 5.0% by weight of the Methyl Sulfonyl Methane;
(11) from about 3.0% by weight to about 5.0% by weight of the Lycium Chinese Herb extract;
(12) from about 6.0% by weight to about 8.0% by weight of the Black Cohosh extract;
(13) from about 1.0% by weight to about 3.0% by weight of the Royal Jelly;
(14) from about 0.5% by weight to about 1.5% by weight of the Scullcap Concentrate extract; and
(15) from about 0.5% by weight to about 1.5% by weight of the Curcubita Pepo Pumpkin seed extract;
further wherein the second diet supplement composition comprises:
(1) from about 20.0% by weight to about 22.0% by weight of the Saw Palmetto berry extract;
(2) from about 14.0% by weight to about 16.0% by weight of the Fenugreek seed extract;
(3) from about 11.0% by weight to about 13.0% by weight of the Chaste Tree berry extract;
(4) from about 12.0% by weight to about 14.0% by weight of the Fennel seed extract;
(5) from about 6.0% by weight to about 8.0% by weight of Methyl Sulfonyl Methane;
(6) from about 8.0% by weight to about 10.0% by weight of the Lycium Chinese Herb extract;
(7) from about 7.0% by weight to about 9.0% by weight of the Black Cohosh extract;
(8) from about 2.0% by weight to about 4.0% by weight of the Royal Jelly;
(9) from about 6.0% by weight to about 8.0% by weight of the Scullcap concentrate extract; and
(10) from about 4.0% by weight to about 6.0% by weight of the Curcubita Pepo Pumpkin seed extract.

12. A system according to claim 11, wherein one or both of the first and second compositions further comprises a pharmaceutically acceptable carrier.

13. A system according to claim 11, wherein the first and second compositions are each in the form of at least one separate and distinct capsule or tablet.

14. A method of enhancing breasts of a human female, comprising:
(a) orally administering to the female on a daily basis during a first period of time an effective daily dosage of a first diet supplement composition comprising:
(1) an effective amount of a Blessed Thistle extract;
(2) an effective amount of a Hops extract;
(3) an effective amount of a Wild Yam extract;
(4) an effective amount of a Fenugreek seed extract;
(5) an effective amount of a Saw Palmetto berry extract;
(6) an effective amount of a Chaste Tree berry extract;
(7) an effective amount of a Fennel seed extract;
(8) an effective amount of a Damiana extract;

(9) an effective amount of a Dong Quai extract;
(10) an effective amount of Methyl Sulfonyl Methane;
(11) an effective amount of a Lycium Chinese Herb extract;
(12) an effective amount of a Black Cohosh extract;
(13) an effective amount of Royal Jelly;
(14) an effective amount of a Scullcap Concentrate extract; and
(15) an effective amount of a Curcubita Pepo Pumpkin seed extract; and (b) orally administering to the female on a daily basis during a second period of time an effective daily dosage of a second diet supplement composition comprising:
(1) an effective amount of a Saw Palmetto berry extract;
(2) an effective amount of a Fenugreek seed extract;
(3) an effective amount of a Chaste Tree berry extract;
(4) an effective amount of a Fennel seed extract;
(5) an effective amount of Methyl Sulfonyl Methane;
(6) an effective amount of a Lycium Chinese Herb extract;
(7) an effective amount of a Black Cohosh extract;
(8) an effective amount of Royal Jelly;
(9) an effective amount of a Scullcap Concentrate extract; and
(10) an effective amount of a Curcubita Pepo Pumpkin seed extract;
wherein the second diet supplement composition is administered independently of the first diet supplement composition, further wherein the second period of time is subsequent to the first period of time.

15. A method according to claim 14, wherein the first diet supplement composition comprises:
(1) from about 12.0% by weight to about 14.0% by weight of the Blessed Thistle extract;
(2) from about 12.0% by weight to about 14.0% by weight of the Hops extract;
(3) from about 10.0% by weight to about 12.0% by weight of the Wild Yam extract;
(4) from about 8.0% by weight to about 10.0% by weight of the Fenugreek seed extract;
(5) from about 8.0% by weight to about 10.0% by weight of the Saw Palmetto berry extract;
(6) from about 7.0% by weight to about 9.0% by weight of the Chaste Tree berry extract;
(7) from about 7.0% by weight to about 9.0% by weight of the Fennel seed extract;
(8) from about 6.0% by weight to about 8.0% by weight of the Damiana extract;
(9) from about 4.0% by weight to about 6.0% by weight of the Dong Quai extract;
(10) from about 3.0% by weight to about 5.0% by weight of Methyl Sulfonyl Methane;
(11) from about 3.0% by weight to about 5.0% by weight of the Lycium Chinese Herb extract;
(12) from about 6.0% by weight to about 8.0% by weight of the Black Cohosh extract;
(13) from about 1.0% by weight to about 3.0% by weight of Royal Jelly;
(14) from about 0.5% by weight to about 1.5% by weight of the Scullcap Concentrate extract; and
(15) from about 0.5% by weight to about 1.5% by weight of the Curcubita Pepo Pumpkin seed extract;
further wherein the second diet supplement composition comprises:

(1) from about 20.0% by weight to about 22.0% by weight of the Saw Palmetto berry extract;
(2) from about 14.0% by weight to about 16.0% by weight of the Fenugreek seed extract;
(3) from about 11.0% by weight to about 13.0% by weight of the Chaste Tree berry extract;
(4) from about 12.0% by weight to about 14.0% by weight of the Fennel seed extract;
(5) from about 6.0% by weight to about 8.0% by weight of Methyl Sulfonyl Methane;
(6) from about 8.0% by weight to about 10.0% by weight of the Lycium Chinese Herb extract;
(7) from about 7.0% by weight to about 9.0% by weight of the Black Cohosh extract;
(8) from about 2.0% by weight to about 4.0% by weight of Royal Jelly;
(9) from about 6.0% by weight to about 8.0% by weight of the Scullcap concentrate extract; and
(10) from about 4.0% by weight to about 6.0% by weight of the Curcubita Pepo Pumpkin seed extract.

16. A method according to claim 14, wherein the first period of time is about two months, and the second period of time is about four months.

17. A method according to claim 14, wherein the first and second diet supplement compositions are each in the form of at least one separate and distinct tablet or capsule.

18. A method of enhancing breasts of a human female, comprising concurrently executing steps (a) and (b) below:
(a) topically administering to the breasts of the female a daily dosage of a composition comprising:
(1) an effective amount of a Saw Palmetto berry extract;
(2) an effective amount of a Chaste Tree berry extract;
(3) an effective amount of a Fenugreek seed extract;
(4) an effective amount of a Fennel seed extract;
(5) an effective amount of a Comfrey extract;
(6) an effective amount of a White Willow Bark extract;
(7) an effective amount of a Ma Huang extract;
(8) an effective amount of a Black Cohosh extract;
(9) an effective amount of a Guarana extract;
(10) an effective amount of a Passion Flower extract;
(11) an effective amount of a Bilberry extract;
(12) an effective amount of a Horsetail extract; and
(13) an effective amount of a Cayenne extract,
wherein the composition is applied for a first effective period of time; and (b) orally and separately administering to the female on a daily basis an effective daily dosage of a first diet supplement composition and an effective daily dosage of a second diet supplement composition, wherein the first diet supplement composition is administered during a second period of time concurrent with the first period of time, and the second diet supplement composition is administered during a third period of time which is subsequent to the second period of time, further wherein the first diet supplement composition contains:
(1) an effective amount of a Blessed Thistle extract;
(2) an effective amount of a Hops extract;
(3) an effective amount of a Wild Yam extract;
(4) an effective amount of a Fenugreek seed extract;
(5) an effective amount of a Saw Palmetto berry extract;
(6) an effective amount of a Chaste Tree Berry extract;
(7) an effective amount of a Fennel seed extract;
(8) an effective amount of a Damiana extract;
(9) an effective amount of a Dong Quai extract;
(10) an effective amount of Methyl Sulfonyl Methane;

(11) an effective amount of a Lycium Chinese Herb extract;
(12) an effective amount of a Black Cohosh extract;
(13) an effective amount of Royal Jelly;
(14) an effective amount of a Scullcap Concentrate extract; and
(15) an effective amount of a Curcubita Pepo Pumpkin seed extract; and
further wherein the second diet supplement composition contains:
(1) an effective amount of a Saw Palmetto berry extract;
(2) an effective amount of a Fenugreek seed extract;
(3) an effective amount of a Chaste Tree berry extract;
(4) an effective amount of a Fennel seed extract;
(5) an effective amount of Methyl Sulfonyl Methane;
(6) an effective amount of a Lycium Chinese Herb extract;
(7) an effective amount of a Black Cohosh extract;
(8) an effective amount of Royal Jelly;
(9) an effective amount of a Scullcap Concentrate extract; and
(10) an effective amount of a Curcubita Pepo Pumpkin seed extract.

* * * * *